(12) United States Patent
Hotter et al.

(10) Patent No.: US 8,785,455 B2
(45) Date of Patent: Jul. 22, 2014

(54) POLYMORPH OF LINAGLIPTIN BENZOATE

(75) Inventors: Andreas Hotter, Kundl (AT); Arthur Pichler, Kundl (AT)

(73) Assignee: Sandoz AG, Basel (CH)

( * ) Notice: Subject to any disclaimer, the term of this patent is extended or adjusted under 35 U.S.C. 154(b) by 0 days.

(21) Appl. No.: 14/115,880

(22) PCT Filed: May 9, 2012

(86) PCT No.: PCT/EP2012/058556
§ 371 (c)(1),
(2), (4) Date: Jan. 17, 2014

(87) PCT Pub. No.: WO2012/152837
PCT Pub. Date: Nov. 15, 2012

(65) Prior Publication Data
US 2014/0121225 A1   May 1, 2014

(30) Foreign Application Priority Data

May 10, 2011   (EP) ..................................... 11165597

(51) Int. Cl.
*A61K 31/522*   (2006.01)
*C07D 473/04*   (2006.01)

(52) U.S. Cl.
USPC ..................................... 514/263.21; 544/268

(58) Field of Classification Search
USPC ..................................... 544/268; 514/263.21
See application file for complete search history.

(56) References Cited

FOREIGN PATENT DOCUMENTS

| EP | 1532149 B1 | 8/2003 |
|----|-----------|--------|
| EP | 2023902 B1 | 4/2007 |
| WO | 2007/128721 A1 | 11/2007 |
| WO | 2010/072776 A1 | 7/2010 |

*Primary Examiner* — Kristin Vajda
(74) *Attorney, Agent, or Firm* — Jeffrey S. Melcher; Manelli Selter PLLC

(57) ABSTRACT

The present invention relates to a novel polymorph of Linagliptin benzoate and to methods for its preparation. Furthermore the present invention relates to the use of the novel polymorph for the preparation of a medicament. In addition the present invention relates to pharmaceutical compositions comprising an effective amount of the novel polymorph of Linagliptin benzoate.

18 Claims, 5 Drawing Sheets

POLYMORPH OF LINAGLIPTIN BENZOATE

FIELD OF THE INVENTION

The present invention relates to a novel polymorph of Linagliptin benzoate and to methods for its preparation. Furthermore the present invention relates to the use of the novel polymorph for the preparation of a medicament. In addition the present invention relates to pharmaceutical compositions comprising an effective amount of the novel polymorph of Linagliptin benzoate. Moreover the present invention relates to a pharmaceutical combination comprising an effective amount of the novel polymorph of Linagliptin benzoate and Metformin.

BACKGROUND OF THE INVENTION

Linagliptin, also called 8-[(3R)-3-Amino-1-piperidinyl]-7-(2-butyn-1-yl)-3,7-dihydro-3-methyl-1-[(4-methyl-2-quinazolinyl)methyl]-1H-purine-2,6-dione, acts as a dipeptidyl peptidase IV inhibitor and is intended to be used for the once-daily oral treatment of type 2 diabetes. In the third quarter 2010, regulatory filings were submitted in the USA, EU and Japan for the approval of Linagliptin for the treatment of diabetes and in the $3^{rd}$ quarter 2011 Linagliptin received FDA approval.

The chemical structure of Linagliptin is represented by the following formula I

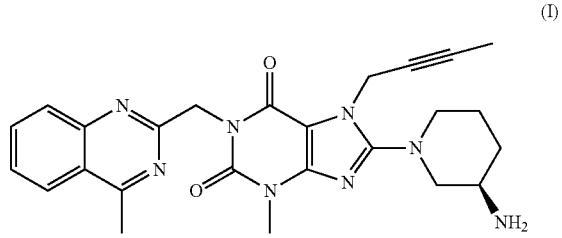 [SMILES: CC#CCn1c(N2CCC[C@@H](N)C2)nc2c1c(=O)n(Cc1nc(C)c3ccccc3n1)c(=O)n2C]

(I)

EP1532149 B1 discloses the compound Linagliptin per se and physiologically acceptable salts with inorganic or organic acids thereof.

WO2007/128721 A1 describes crystalline forms A, B, C, D and E of Linagliptin free base. WO2010/072776 A1 describes crystalline acid addition salts of Linagliptin such as the benzoate. In said patent application Linagliptin benzoate is characterized by an X-ray powder diffractogram and a melting point of about 155° C. measured by DSC at defined conditions. Polymorphism is a phenomenon relating to the occurrence of different crystal forms for one molecule. There may be several different crystalline forms for the same molecule with distinct crystal structures and varying in physical properties like melting point, XRPD spectrum and IR-spectrum. These polymorphs are thus distinct solid forms which share the molecular formula of the compound from which the crystals are made up, however they may have distinct advantageous physical properties which can have a direct effect on the ability to process and/or manufacture the drug substance, like flowability, and the drug product, like flowability, as well as on drug product stability, dissolution, and bioavailability.

These distinct physical properties of different polymorphs of the same compound can render different polymorphs more, or less, useful for a particular purpose, such as for pharmaceutical formulation.

The present inventors have discovered that the crystalline form of Linagliptin benzoate of WO2010/072776 A1 is quite hygroscopic. Hygroscopic compounds, however, are difficult to handle under common pharmaceutical processing conditions, such as wet granulation, and they ask for special techniques and equipment in order to avoid e.g. chemical degradation or polymorphic transformation during processing. Furthermore, hygroscopic compounds—and the pharmaceutical compositions containing them—must often be packaged into special containments in order to ensure proper product quality during storage.

Crystal forms of Linagliptin benzoate with better processability for favored formulation conditions, like wet granulation, would facilitate the production of pharmaceutical compositions comprising Linagliptin. There is thus a need for solid forms of Linagliptin which avoid one or more problems of the known Linagliptin benzoate form I.

SUMMARY OF THE INVENTION

The inventors of the present invention have found a novel polymorphic form of Linagliptin benzoate, in the following named Linagliptin benzoate form II, which is significantly less hygroscopic than the crystalline Linagliptin benzoate described in WO2010/072776 A1 and which is thus easier to handle under typical pharmaceutical processing conditions, such as wet granulation, than the Linagliptin benzoate of WO2010/072776 A1, in the following named Linagliptin benzoate form I. In particular, Linagliptin benzoate form II enables standard pharmaceutical processing conditions to be used, such as work in an atmosphere having a relative humidity of about 0 to 90% relative humidity. Furthermore Linagliptin benzoate form II needs not to be packaged into special containments for proper product quality during storage to be achieved.

The present invention thus relates to a novel polymorph of Linagliptin benzoate, in the following named Linagliptin benzoate form II. Form II of Linagliptin benzoate can be characterized by showing an XRPD pattern comprising characteristic peaks at 2-theta angles of 8.0±0.2°, 8.7±0.2°, 10.4±0.2°, 12.9±0.2°, 13.8±0.2° and 17.4±0.2°.

In a further embodiment the present invention also relates to a process of preparing Linagliptin benzoate form II comprising the steps of
a) dissolving Linagliptin benzoate in acetonitrile upon heating,
b) optionally filtering the solution,
c) slowly cooling the solution in order to induce crystallization starting at above 35° C.,
d) isolating the obtained crystals and
e) optionally drying the crystals.

In another embodiment the present invention relates to the use of Linagliptin benzoate form II for the preparation of a medicament.

In addition the present invention relates to a pharmaceutical composition comprising an effective amount of Linagliptin benzoate form II.

In the context of the present invention the following abbreviations have the indicated meaning, unless explicitly stated otherwise:
XRPD: Powder X-ray diffraction
FTIR: Fourier transformation infrared spectrum
r.h. or RH: relative humidity
r.t.: room temperature
DSC: Differential scanning calorimetry Δm_TR: Weight change of the sample (determined by Karl Fischer titration)

DETAILED DESCRIPTION OF THE INVENTION

In a first aspect, the present invention relates to a novel and advantageous crystalline form of Linagliptin benzoate (hereinafter also referred to as Linagliptin benzoate form II).

Linagliptin benzoate form II can be characterized by showing an XRPD pattern comprising characteristic peaks at 2-theta angles of 8.0±0.2°, 8.7±0.2°, 10.4±0.2°, 12.9±0.2°, 13.8±0.2° and 17.4±0.2°.

Preferably, Linagliptin benzoate form II can be characterized by an XRPD pattern comprising characteristic peaks and intensities as shown in the following table:

| Position [°2-theta] | Relative Intensity [%] |
|---|---|
| 8.0 ± 0.2 | 100 |
| 8.7 ± 0.2 | 23 |
| 10.4 ± 0.2 | 14 |
| 12.9 ± 0.2 | 38 |
| 13.8 ± 0.2 | 30 |
| 17.4 ± 0.2 | 14 |

More preferably, further peaks may be found at 2-theta angles of 5.2±0.2°, 6.7±0.2°, 12.4±0.2°, 15.7±0.2°, 18.8±0.2°, 20.3±0.2°, 22.2±0.2°, 23.3±0.2° and 24.5±0.2°.

Even more preferably, Linagliptin benzoate form II can be characterized by an XRPD pattern comprising characteristic peaks and intensities as shown in the following table:

| Position [°2-theta] | Relative Intensity [%] |
|---|---|
| 5.2 ± 0.2 | 3 |
| 6.7 ± 0.2 | 7 |
| 8.0 ± 0.2 | 100 |
| 8.7 ± 0.2 | 23 |
| 10.4 ± 0.2 | 14 |
| 12.4 ± 0.2 | 6 |
| 12.9 ± 0.2 | 38 |
| 13.8 ± 0.2 | 30 |
| 15.7 ± 0.2 | 9 |
| 17.4 ± 0.2 | 14 |
| 18.8 ± 0.2 | 8 |
| 20.3 ± 0.2 | 5 |
| 22.2 ± 0.2 | 9 |
| 23.3 ± 0.2 | 7 |
| 24.5 ± 0.2 | 5 |

Figure 1:
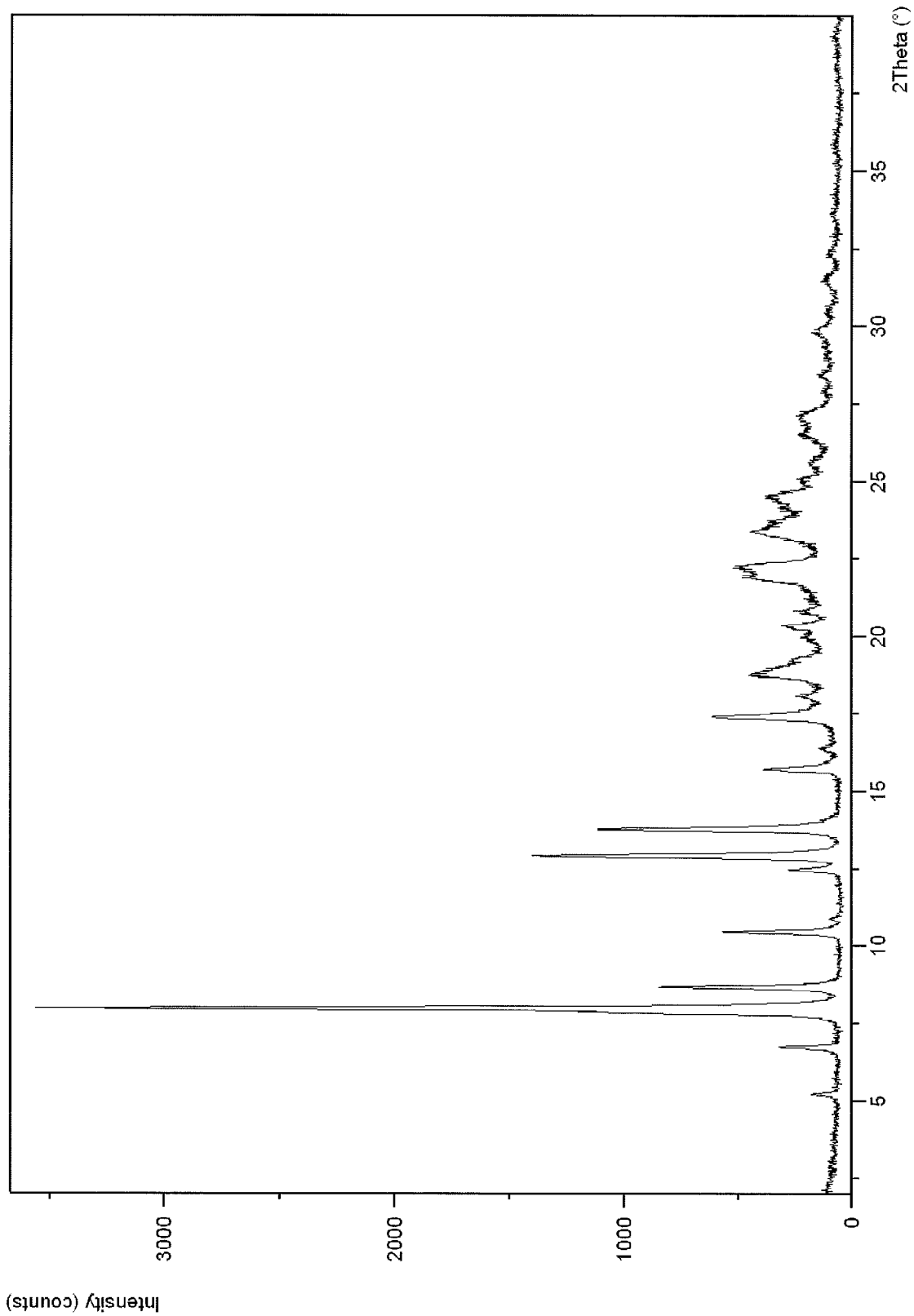
FIG. 1: X-ray powder diffraction (XRPD) pattern of Linagliptin benzoate form II

An illustrative XRPD pattern of Linagliptin benzoate form II is shown in FIG. 1.

Figure 2:
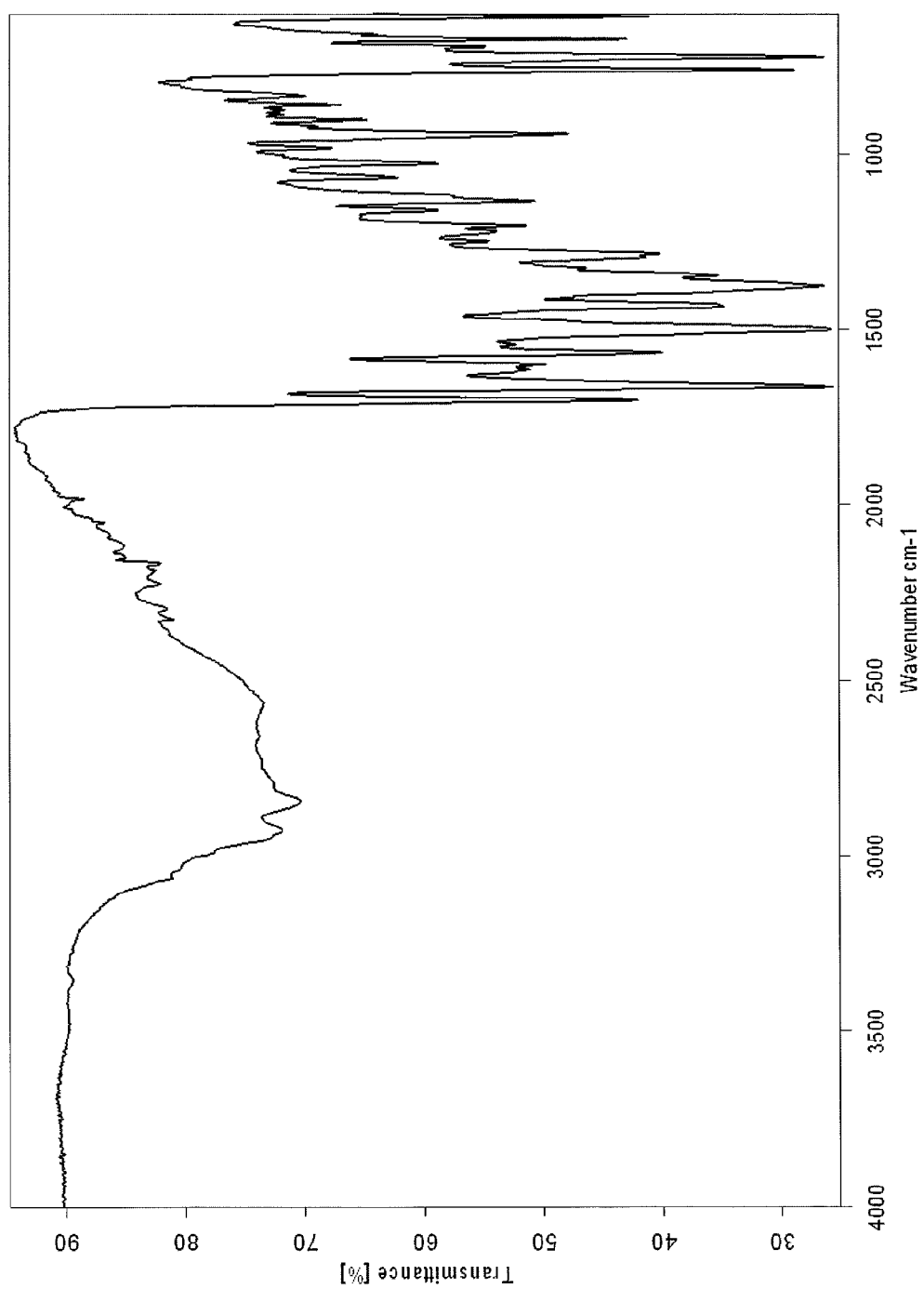
FIG. 2: Fourier transformation infrared spectrum (FTIR) of Linagliptin benzoate form II

Linagliptin benzoate form II may further be characterized by an FTIR spectrum comprising characteristic peaks at 1701±2 $cm^{-1}$, 1663±2 $cm^{-1}$, 1134±2 $cm^{-1}$, 760±2 $cm^{-1}$ and 724±2 $cm^{-1}$. Preferably, further peaks may be found at wavenumbers of 2925±2 $cm^{-1}$, 2841±2 $cm^{-1}$, 1600±2 $cm^{-1}$, 1566±2 $cm^{-1}$, 1499±2 $cm^{-1}$, 1434±2 $cm^{-1}$, 1376±2 $cm^{-1}$, 1346±2 $cm^{-1}$, 1285±2 $cm^{-1}$, 1203±2 $cm^{-1}$, 1159±2 $cm^{-1}$, 1066±2 $cm^{-1}$, 1026±2 $cm^{-1}$, 982±2 $cm^{-1}$, 942±2 $cm^{-1}$, 902±2 $cm^{-1}$, 859±2 $cm^{-1}$, 835±2 $cm^{-1}$, 672±2 $cm^{-1}$ and 609±2 $cm^{-1}$. An illustrative FTIR spectrum is shown in FIG. 2.

Figure 3:
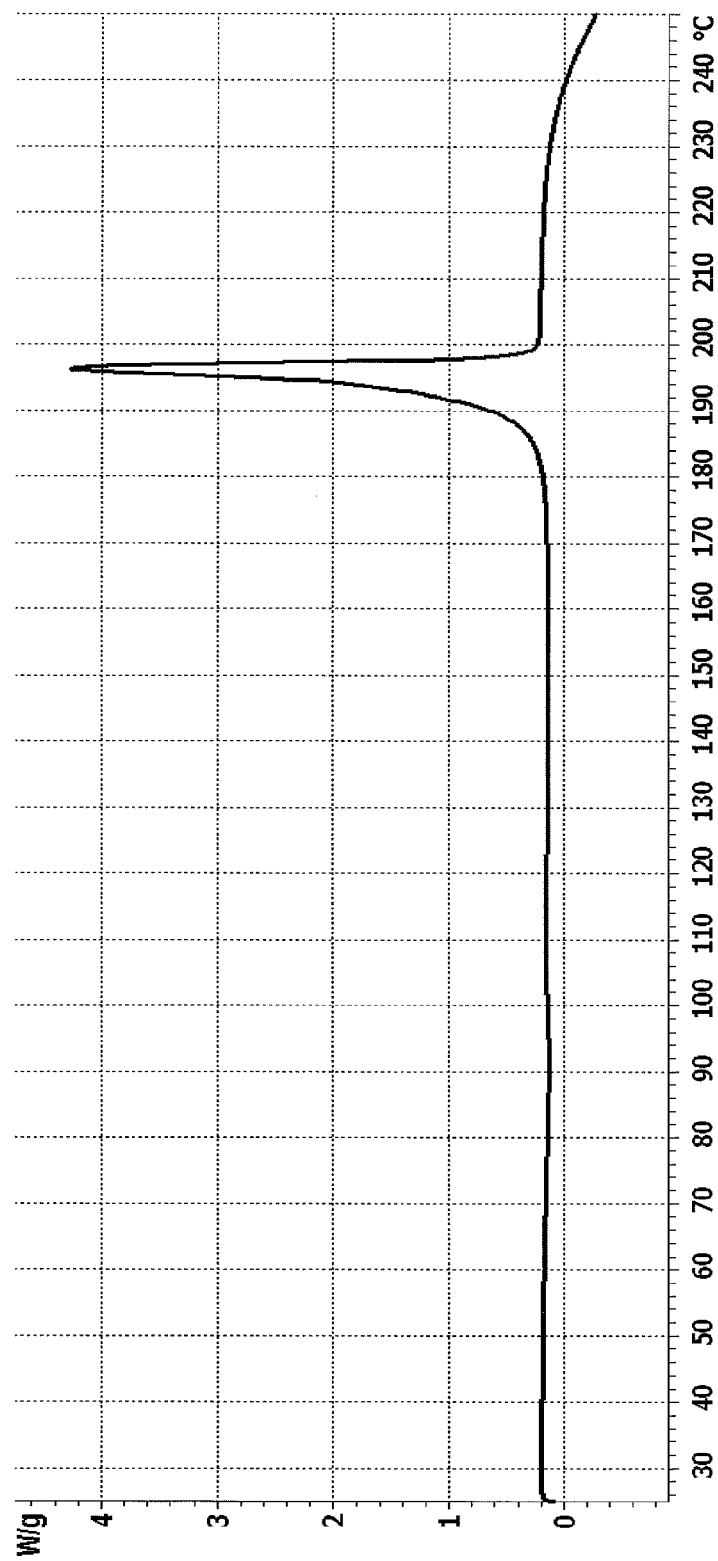
FIG. 3: Differential scanning calorimetric (DSC) curve of Linagliptin benzoate form II

Linagliptin benzoate form II may further be described by differential scanning calorimetric analysis. The DSC curve shows a single melting endotherm with an onset temperature of about 193° C. An illustrative DSC curve is shown in FIG. 3.

Figure 4:
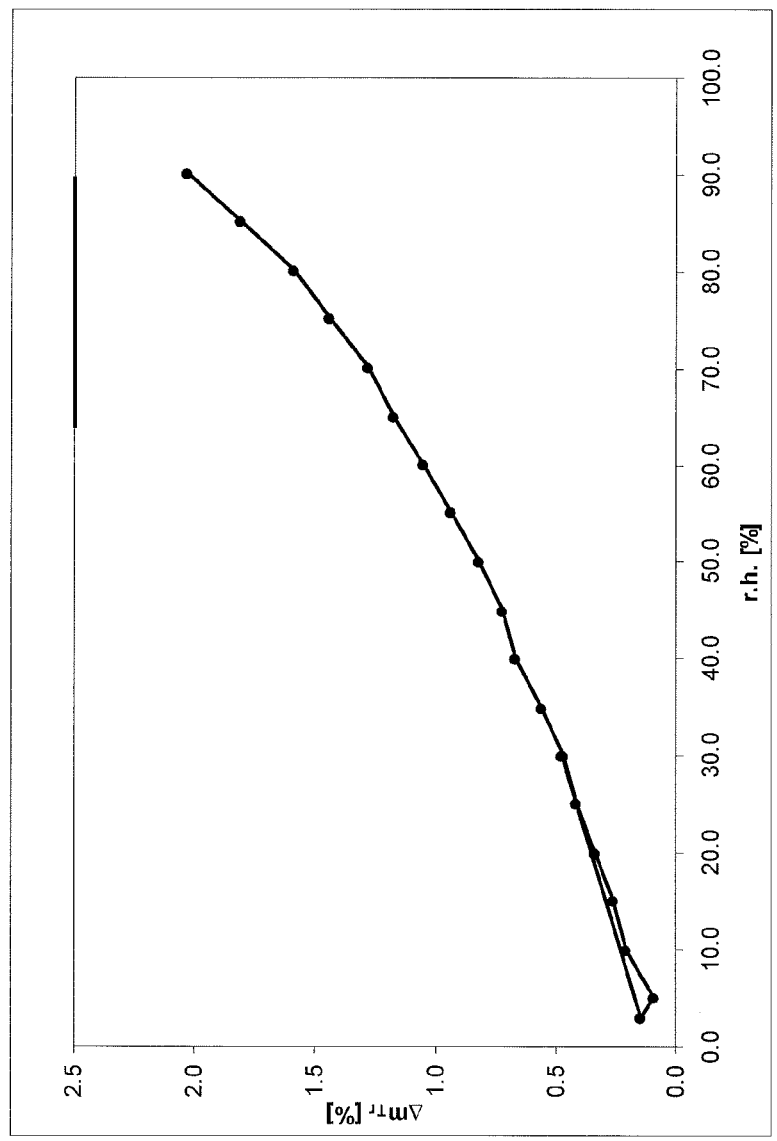
FIG. 4: Moisture sorption isotherm of Linagliptin benzoate form II
Figure 5:
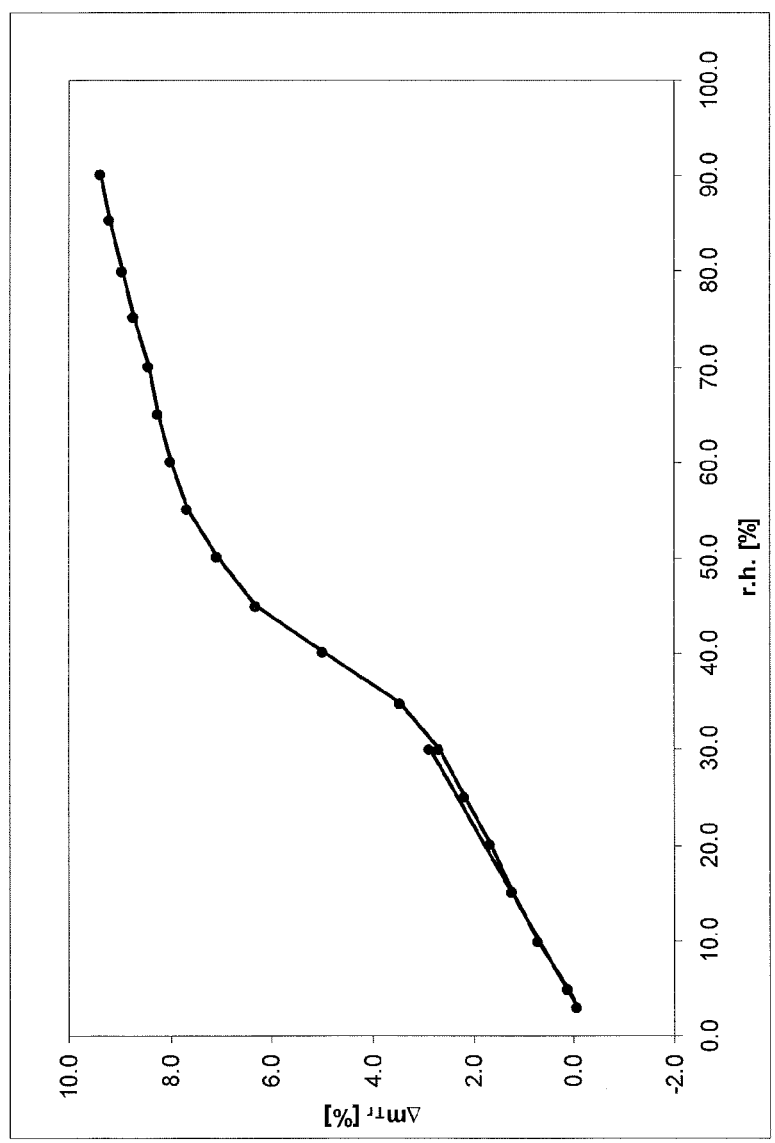
FIG. 5: Moisture sorption isotherm of Linagliptin benzoate form I of WO2010/072776 A1

Linagliptin benzoate form II is significantly less hygroscopic than crystalline Linagliptin benzoate of WO2010/072776 A1, as can readily be seen by a comparison of FIGS. 4 and 5, and is therefore very suitable for pharmaceutical formulation, for example for use in a wet granulation process for the production of pharmaceutical compositions comprising Linagliptin. Moreover, Linagliptin benzoate form II is more stable than form I upon storage at conditions of high relative humidity.

The present invention also relates to a process for the preparation of Linagliptin benzoate form II. Linagliptin benzoate form II may be prepared by a process comprising the steps of
  a) dissolving Linagliptin benzoate in acetonitrile upon heating, for example from 50° C. to 82° C.,
  b) optionally filtering the solution,
  c) slowly cooling the solution in order to induce crystallization at above 35° C.,
  d) isolating the obtained crystals and
  e) optionally drying the crystals.

In step a) any form of Linagliptin benzoate may be used as starting material, e.g. amorphous Linagliptin benzoate, crystalline Linagliptin benzoate or a mixture of amorphous and crystalline Linagliptin benzoate. A crystalline form of Linagliptin benzoate suitable as starting material is e.g. described in WO2010/072776 A1. The starting material Linagliptin benzoate may be solubilized in acetonitrile. Typically it is the target to achieve Linagliptin benzoate concentrations after step a) ranging from about 10 g/l to 20 g/l. The dissolution temperature depends on the initial amount of Linagliptin benzoate added to the acetonitrile and thus the concentration to be achieved after dissolution and may range from about 63° C. (for example 10 g of solid Linagliptin benzoate added per liter of acetonitrile to achieve a concentration of about 10 g/L after dissolution) to about 82° C. (for example when 20 g of solid Linagliptin benzoate are added per liter of acetonitrile to achieve a concentration of about 20 g/L after dissolution). The obtained solution may optionally be filtered as step b) in order to remove any undissolved particles.

In step c) the crystallization of Linagliptin benzoate form II can be initiated by slowly cooling the obtained solution to about −70 to 50° C., preferably to about −40 to about 40° C., more preferably to about −20 to about 25° C. and most preferably the solution is slowly cooled to 25° C. Slowly cooling in this context means that the cooling rate is ≤−1° C./min, preferably from −1° C./min to −0.1° C./min, more preferably from −0.8° C./min to −0.4° C./min.

After the cooling step the obtained suspension may be further stirred for about 6 to 72 hours, more preferably for about 6 to 48 hours and most preferably for about 6 to 24 hours.

Thereafter the crystals can be isolated by any conventional method such as filtration, centrifugation or evaporation of the solvent.

Finally the obtained Linagliptin benzoate form II can be dried preferably under vacuum at a temperature preferably ranging from about 25-100° C., more preferably from about 40-90° C. and most preferably the material is dried at about 60-80° C. for a time sufficient for drying, for example ranging preferably from about 1-72 hours, more preferably from about 6-48 hours and most preferably from about 12-24 hours.

According to the present process Linagliptin benzoate form II is obtained as spherulitic particles. Such particles show the appearance of a sphere-shaped mass with needles radiating from the centre at a magnification of about 100× in a light microscope. The outer diameter of the spherulitic particles typically ranges from about 10 to 100 μm, more preferably from about 30 to 80 μm and most preferably from about 40 to 60 μm.

Surprisingly Linagliptin benzoate form II of the present invention is only obtained consistently at a crystallization temperature above 35° C. This means that crystallization starts at a temperature above 35° C., as can be detected by the first visible appearance of solid particles in the solution as its temperature slowly decreases. Typically, it is very evident to the skilled person when crystallization starts and thus the crystallization temperature can be readily determined. Starting crystallization at lower temperatures does not lead to Linagliptin benzoate form II in a consistent manner.

In order to best ensure crystallization above about 35° C., a solution having a Linagliptin benzoate concentration of 10 g/l should be applied and the cooling rate should be ≤−1° C./min. Once crystallization has started above about 35° C. Linagliptin benzoate form II is obtained and remains stable also on further cooling.

Surprisingly Linagliptin benzoate form II of the present invention is less hygroscopic than crystalline Linagliptin benzoate of WO2010/072776 A1. Form II only takes up about 2.0 w % water from about 3 to 90% relative humidity at about 25° C., whereas crystalline Linagliptin benzoate of WO2010/072776 A1 takes up about 9.5 w % water from about 3 to 90% relative humidity at about 25° C. In this context w % means the weight % age of water in relation to the total weight.

Moreover, Linagliptin benzoate form II is easier to handle than form I of WO2010/072776 A1 under pharmaceutical processing conditions such as wet granulation. For example, when the granulation liquid is e.g. a solution of a binder, such as copovidone in water, and a premix of Linagliptin benzoate with a diluent, such as mannitol, and a disintegrant, such as pregelatinized starch, is moistened and subsequently granulated with the granulation liquid, the Linagliptin benzoate form II of the present invention has advantages over form I. Furthermore, Linagliptin benzoate form II does not require special techniques such as dry granulation and/or special equipment to be applied during processing. Furthermore Linagliptin benzoate form II shows no requirement for special packaging of form II or pharmaceutical compositions comprising form II, during storage.

Linagliptin benzoate form II of the invention as described above may advantageously be employed in various pharmaceutical formulations for use in the treatment of type 2 diabetes and related diseases in accordance with the present invention. The present invention therefore also relates to a pharmaceutical composition which comprises Linagliptin benzoate form II as described above and a pharmaceutically acceptable carrier.

Preferably, the present invention relates to pharmaceutical compositions, wherein more than 95% of Linagliptin benzoate is stably present as Linagliptin benzoate form II, more preferably wherein Linagliptin benzoate form II is the only detectable crystalline form of Linagliptin benzoate. The absence of other polymorphic forms of Linagliptin benzoate, such as form I, can be tested by comparing an XRPD taken of any crystalline Linagliptin benzoate with the XRPD of form II as obtained e.g. from example 1 and shown in FIG. 1, which for this comparison is to be taken as an XRPD of 100% form.

"Stably present" as defined herein means that even after storage of the pharmaceutical composition for 180 days, and preferably even after storage for 3 years, the crystalline form of Linagliptin benzoate designated as Linagliptin benzoate form II initially comprised in the pharmaceutical composition is still present as Linagliptin benzoate form II after storage for the indicated period.

The pharmaceutical compositions of the invention comprising Linagliptin benzoate form II may further comprise one or more pharmaceutically acceptable excipients. Such excipients are preferably selected from the group consisting of fillers, sweeteners, buffering agents, glidants, flowing agents, flavouring agents, lubricants, preservatives, surfactants, wetting agents, binders, disintegrants and thickeners. Other excipients known in the field of pharmaceutical compositions may also be used. Furthermore, the pharmaceutical composition may comprise a combination of two or more excipients also within one of the members of the above mentioned group.

Examples of suitable excipients for pharmaceutical compositions of the invention comprising Linagliptin benzoate form II are given e.g. in EP2023902 B1, which is herein incorporated by reference, in paragraphs [0005] to [0011].

Paragraphs [0005] and [0006] of EP2023902 B1 disclose examples of suitable diluents for the pharmaceutical compositions of the present invention comprising Linagliptin benzoate form II. The preferred diluents, which can also be used for the pharmaceutical compositions of the present invention, are e.g. cellulose powder, dibasic calciumphosphate anhydrous, dibasic calciumphosphate dihydrate, erythritol, low substituted hydroxypropyl cellulose, mannitol, pregelatinized starch, low substituted hydroxypropylcellulose or xylitol, whereas mannitol and pregelatinized starch are preferred.

Paragraph [0007] of EP2023902 B1 discloses examples of lubricants for the pharmaceutical compositions of the present invention comprising Linagliptin benzoate form II. The preferred lubricants, which can also be used for the pharmaceutical compositions of the present invention, are e.g. talc, polyethyleneglycol, calcium behenate, calcium stearate, hydrogenated castor oil or magnesium stearate, whereas magnesium stearate is preferred.

Paragraph [0008] of EP2023902 B1 discloses examples of binders for the pharmaceutical compositions of the present invention comprising Linagliptin benzoate form II. The preferred binders, which can also be used for the pharmaceutical compositions of the present invention, are e.g. copovidone, hydroxypropyl methylcellulose, hydroxypropylcellulose, polyvinylpyrrolidone, gregelatinized starch, low-substituted hydroxypropylcellulose, whereas copovidone and pregelatinized starch are preferred.

Paragraph [0010] of EP2023902 B1 discloses examples of disintegrants for the pharmaceutical compositions of the present invention comprising Linagliptin benzoate form II. The preferred disintegrants, which can also be used for the pharmaceutical compositions of the present invention, are e.g. corn starch, crospovidone, low-substituted hydroxypropylcellulose or pregelatinized starch, whereas corn starch is preferred.

Paragraph [0011] of EP2023902 B1 discloses an example of an optional glidant for the pharmaceutical compositions of the present invention comprising Linagliptin benzoate form II. The optional glidant, which can also be used for the pharmaceutical compositions of the present invention is silicon dioxide.

Examples of suitable processes for the preparation of the pharmaceutical compositions of the present invention are given e.g. in EP2023902 B1, which is herein incorporated by reference, in paragraphs [0019] to [0026], wherein it is to be understood that whenever the terms active ingredient or DPP-IV inhibitor are used in EP2023902 B1 an equivalent amount of Linagliptin benzoate form II (amount relating to Linagliptin free base) of the present invention is to be used.

Concrete examples for the production of formulations of the present invention are given e.g. in EP2023902 B1, paragraphs [0027] to [0040]. These examples can be repeated using Linagliptin benzoate form II of the present invention.

Formulations of the present invention typically comprise 0.1 to 100 mg of Linagliptin benzoate form II, whereas preferred dosages are 0.5 mg, 1 mg, 2.5 mg, 5 mg and 10 mg (calculated as free base).

As discussed above, one advantage of form II of the present invention is that it is less hygroscopic than form I. Thus, Linagliptin benzoate form II of the present invention enables the skilled person to package or fill pharmaceutical compositions comprising Linagliptin benzoate form II of the present invention into inexpensive containers or blisters.

The present invention therefore also relates to a container comprising pharmaceutical compositions comprising Linagliptin benzoate form II of the present invention, in particular to a container prepared from a material having a permeability for water vapor as measured according to DIN 53 122 at a foil thickness of 50 µm of from $1.0$ $g*m^{-2}*d^{-1}$ to 5000 $g*m^{-2}*d^{-1}$, more preferably of from 5 $g*m^{-2}*d^{-1}$ to 2000 $g*m^{-2}*d^{-1}$. Preferred examples of such an inexpensive packaging material with relatively high permeability for water vapor are polyvinylchloride, polystyrole, polyamide, polyethylenevinylacetate, cellophane and celluloseacetate. The use of these materials for blistering the pharmaceutical compositions comprising Linagliptin benzoate form II becomes possible due to the low hygroscopicity of form II of the invention. This represents a clear economic advantage of the Linagliptin benzoate form II of the invention.

The present invention also relates to the use of Linagliptin benzoate form II for the production of a pharmaceutical composition intended for sale in a tropical country having areas with an Af or Am climate according to the Köppen-Geiger climate classification. In a further preferred embodiment the present invention relates to a container prepared from a material having a permeability for water vapor as measured according to DIN 53 122 at a foil thickness of 50 µm of from $1.0 g*m^{-2}*d^{-1}$ to $5000 g*m^{-2}*d^{-1}$, more preferably of from 5 $g*m^{-2}*d^{-1}$ to 2000 $g*m^{-2}*d^{-1}$ wherein the pharmaceutical composition is intended for sale in a tropical country having areas with an Af or Am climate according to the Köppen-Geiger climate classification. Preferred examples of inexpensive packaging material with relatively high permeability for water vapor for such a container are polyvinylchloride, polystyrole, polyamide, polyethylenevinylacetate, cellophane and celluloseacetate.

The use of these materials for blistering the pharmaceutical compositions comprising Linagliptin benzoate form II even for the use in countries with humid and moist climate conditions becomes possible due to the low hygroscopicity of form II of the invention. This represents a clear economic advantage of the Linagliptin benzoate form II of the invention.

In a further embodiment the present invention relates to a pharmaceutical combination comprising an effective amount of Linagliptin benzoate form II of the present invention and Metformin or a pharmaceutically acceptable salt thereof. Furthermore the present invention relates to a pharmaceutical combination comprising an effective amount of Linagliptin benzoate form II of the present invention and Pioglitazone or a pharmaceutically acceptable salt thereof. In addition the present invention relates to a pharmaceutical combination comprising an effective amount of Linagliptin benzoate form II of the present invention and a Sulfonylurea or a pharmaceutically acceptable salt thereof.

Moreover the present invention relates to a pharmaceutical combination comprising an effective amount of
  Linagliptin benzoate form II of the present invention and
  a Sulfonylurea or a pharmaceutically acceptable salt thereof and
  Metformin or a pharmaceutically acceptable salt thereof.

The present invention also relates to the above-described container comprising pharmaceutical compositions, comprising a combination of Linagliptin benzoate form II and Metformin or a pharmaceutically acceptable salt thereof; Linagliptin benzoate form II and Pioglitazone or a pharmaceutically acceptable salt thereof; Linagliptin benzoate form II and a Sulfonylurea or a pharmaceutically acceptable salt thereof; and Linagliptin benzoate form II and Metformin or a pharmaceutically acceptable salt thereof and a Sulfonylurea or a pharmaceutically acceptable salt thereof; respectively in particular to a container prepared from a material having a high permeability for water vapor as described above, and/or intended for sale in a tropical country having areas with an Af or Am climate according to the Köppen-Geiger climate classification, as described above.

Other objects, features, advantages and aspects of the present invention will become apparent to those of skill from the following description. It should be understood, however, that the description and the following specific examples, while indicating preferred embodiments of the invention, are given by way of illustration only. Various changes and modifications within the spirit and scope of the disclosed invention will become readily apparent to those skilled in the art from reading the description and the other parts of the present disclosure.

EXAMPLES

The X-ray powder diffraction (XRPD) pattern was obtained with a PANalytical X'Pert PRO diffractometer equipped with a theta/theta coupled goniometer in transmission geometry, Cu—Kα1,2 radiation (wavelength 0.15419 nm) with a focusing mirror and a solid state PIXcel detector. The pattern was recorded at a tube voltage of 45 kV and a tube current of 40 mA, applying a stepsize of 0.013° 2-theta with 80 s per step (255 channels) in the angular range of 2° to 40° 2-theta at ambient conditions. A typical precision of the 2-theta values is in the range of about ±0.2° 2-theta. Thus a diffraction peak that appears at 5.0° 2-theta can appear between 4.8 and 5.2° 2-theta on most X-ray diffractometers under standard conditions.

The infrared spectrum (IR) was recorded on an MKII Golden Gate™ Single Reflection Diamond ATR (attenuated total reflection) cell with a Bruker Tensor 27 FTIR spectrometer with 4 $cm^{-1}$ resolution at ambient conditions. To record a spectrum a spatula tip of a sample was applied to the surface of the diamond in powder form. Then the sample was pressed onto the diamond with a sapphire anvil and the spectrum was recorded. A spectrum of the clean diamond was used as background spectrum. A typical precision of the wavenumber values is in the range of about ±2 cm$^{-1}$. Thus, an infrared peak that appears at 1716 cm$^{-1}$ can appear between 1714 and 1718 cm$^{-1}$.

Differential scanning calorimetry (DSC) was performed on a Mettler Polymer DSC R instrument. 5.3 mg sample were heated in a 40 µl aluminium pan with a pierced aluminium lid from 25 to 250° C. at a rate of 10° C./min. Nitrogen (purge rate 50 ml/min) was used as purge gas.

The water uptake of the crystalline forms of Linagliptin benzoate was determined by dynamic water vapor sorption/desorption. Therefore both forms were conditioned at about 28% relative humidity (RH) and the initial water content was determined by Karl-Fischer-titration. Then a moisture sorption experiment was performed with an SPSx-1µ moisture sorption analyzer (Projekt Messtechnik, Ulm) by stepwise increasing the RH in the range of about 3% RH to about 90% RH within approximately 2.5 days at 25±0.1° C.

Example 1

Preparation of Polymorph II of Linagliptin Benzoate

A suspension of 0.60 g Linagliptin benzoate in 40 ml acetonitrile was heated to reflux (T$_{bath}$=82° C.), whereby a clear solution was obtained. The solution was allowed to cool to about 25° C. within about 90 minutes leading to crystallization at about 60° C. The obtained suspension was further stirred at about 25° C. for about 13 hours before the crystals were isolated by filtration. The crystals were dried at 80° C. under vacuum for about 24 hours to obtain 0.48 g polymorph II of Linagliptin benzoate. Upon characterization of polymorph II of Linagliptin benzoate with XRPD, IR, DSC and water vapor sorption, the results shown in FIGS. 1 to 4 are obtained.

Example 2

Preparation of Polymorph II of Linagliptin Benzoate

A suspension of 0.60 g Linagliptin benzoate in 30 ml acetonitrile was heated to reflux (T$_{bath}$=82° C.), whereby a clear solution was obtained. The solution was allowed to cool to about 25° C. within about 90 minutes leading to crystallization at about 75° C. The obtained suspension was further stirred at about 25° C. for about 5 hours before the crystals were isolated by filtration. The crystals were dried at 80° C. under vacuum for about 15 hours to obtain 0.47 g polymorph II of Linagliptin benzoate.

Comparative Example 1

Preparation of Linagliptin Benzoate

A suspension of 0.60 g Linagliptin benzoate in 40 ml acetonitrile was heated to reflux (T$_{bath}$=82° C.), whereby a clear solution was obtained. The solution was fast cooled by putting the reaction vessel into an ice bath leading to crystallization after about 5 minutes at a temperature of about 0° C. The obtained suspension was further stirred at the ice bath for about 2 hours before the crystals were isolated by filtration. The crystals were dried at 80° C. under vacuum for about 13 hours to obtain 0.44 g Linagliptin benzoate as a mixture of amorphous and crystalline Linagliptin benzoate which was not form II.

Comparative Example 2

Preparation of Linagliptin Benzoate

A suspension of 0.30 g Linagliptin benzoate in 60 ml acetonitrile was heated to reflux (T$_{bath}$=82° C.), whereby a clear solution was obtained. The solution was allowed to cool to about 25° C. within about 90 minutes, but no crystallization occurred. Thus the solution was further stirred on an ice bath leading to crystallization at about 0° C. The obtained suspension was further stirred on the ice bath for about 3.5 hours before the crystals were isolated by filtration. The crystals were dried at 80° C. under vacuum for about 15 hours to obtain 0.14 g Linagliptin benzoate as a mixture of amorphous and crystalline Linagliptin benzoate which was not form II.

Reference Example 1

Preparation of Crystalline Linagliptin Benzoate of WO2010/072776 A1

A mixture of 2.50 g Linagliptin free base in 20 ml isopropanol was heated to reflux. To the hot suspension 646 mg benzoic acid dissolved in 5 ml isopropanol were added. The mixture was allowed to cool to about 25° C. and further stirred at the same temperature for about 7.5 hours. The solid was isolated by filtration and dried at 40° C. for about 13 hours to obtain 2.94 g crystalline Linagliptin benzoate of WO2010/072776 A1, which was confirmed to be Linagliptin benzoate form I by XRPD.

The invention claimed is:
1. A crystalline form of Linagliptin benzoate having an X-ray powder diffraction pattern comprising peaks at 2-theta angles of 8.0±0.2°, 8.7±0.2°, 10.4±0.2°, 12.9±0.2°, 13.8±0.2° and 17.4±0.2°.
2. The crystalline form of Linagliptin benzoate according to claim 1, having an infrared spectrum comprising peaks at wavenumbers of 1701±2 cm$^{-1}$, 1663±2 cm$^{-1}$, 1134±2 cm$^{-1}$, 760±2 cm$^{-1}$ and 724±2 cm$^{-1}$.
3. The crystalline form of Linagliptin benzoate according to claim 1, having a DSC curve showing an endothermic peak with an onset temperature of about 193° C.
4. The crystalline form of Linagliptin benzoate according to claim 1 having a water content of about 0 w % at 3% relative humidity and about 2.0 w % at 90% relative humidity.
5. The crystalline form of Linagliptin benzoate according to claim 1 in the form of spherulitic particles, wherein the outer diameter of the spherulitic particles is from 10 to 100 µm.
6. A process for the preparation of the crystalline form of Linagliptin benzoate according to claim 1 comprising the steps of:
   a) dissolving Linagliptin benzoate in acetonitrile at a concentration ranging from about 10 g/l to 20 g/l upon heating;
   b) optionally filtering the solution;
   c) cooling the solution at a cooling rate of ≤−1° C./min in order to induce crystallization at a temperature above 35° C.;
   d) isolating the obtained crystals; and
   e) optionally drying the crystals.

7. A pharmaceutical composition comprising a crystalline form of Linagliptin benzoate according to claim 1, further comprising at least one pharmaceutically acceptable excipient.

8. The pharmaceutical composition according to claim 7, which is an oral dosage form.

9. The pharmaceutical composition according to claim 7 comprising additionally Metformin, Pioglitazone, a Sulfonylurea, or a pharmaceutically acceptable salt thereof.

10. The pharmaceutical composition according to claim 7 comprising additionally Metformin or a pharmaceutically acceptable salt thereof, and a Sulfonylurea or a pharmaceutically acceptable salt thereof.

11. Method of using a crystalline form of Linagliptin benzoate according to claim 1 for the preparation of a pharmaceutical composition intended for sale in a country having areas with an Af or Am climate according to the Köppen-Geiger climate classification.

12. A process for preparing a pharmaceutical composition comprising the crystalline form of Linagliptin benzoate according to claim 1, comprising the step of:

mixing the crystalline form of Linagliptin benzoate according to claim 1 with at least one pharmaceutically acceptable excipient.

13. The process of claim 12, wherein mixing is effected by wet granulation.

14. A container comprising a pharmaceutical composition according to claim 7, wherein the container is prepared from a material having a permeability for water vapor as measured according to DIN 53122 of from 1.0 $g*m^{-2}*d^{-1}$ to 5000 $g*m^{-2}*d^{-1}$.

15. The container of claim 14, which is a blister package comprising an oral dosage form, wherein the blister is made from a material selected from the group consisting polyvinylchloride, polystyrole, polyamide, polyethylenevinylacetate, cellophane, celluloseacetate, and any combinations thereof.

16. The pharmaceutical composition according to claim 7, which is an oral dosage form of a capsule or tablet.

17. The pharmaceutical composition according to claim 9, which is an oral dosage form of a capsule or tablet.

18. The pharmaceutical composition according to claim 10, which is an oral dosage form of a capsule or tablet.

* * * * *